United States Patent [19]

Kortright et al.

[11] Patent Number: 4,888,290

[45] Date of Patent: Dec. 19, 1989

[54] MONOCLONAL ANTIBODY SPECIFIC TO HIV ANTIGENS

[75] Inventors: Kenneth H. Kortright, Cooper; David E. Hofheinz; Carole Sullivan, both of Miami; Gary P. Toedter, Miramar, all of Fla.

[73] Assignee: Coulter Corporation

[21] Appl. No.: 118,145

[22] Filed: Nov. 6, 1987

[51] Int. Cl.$^4$ .................. C12N 15/00; G01N 33/567; G01N 33/577

[52] U.S. Cl. .................................. 435/240.27; 435/5; 435/70.21; 435/172.2; 540/387; 540/808; 540/809; 935/110

[58] Field of Search ............. 435/5, 68, 172.2, 240.27; 530/382

[56] References Cited

PUBLICATIONS

Hattori et al., "Characterization of Three Monoclonal Antibodies (VAK3-5) That Identify p24, Core Protein of Human Immunodeficiency Virus, and its Precursors", Jpn. J. Cancer Res. (Gann), 78 (1987) 235–241.

Caruso et al., "Liquid Competition Radioimmunoassay for the Detection and Quantitation of the HIV p24", J. Virol. Meth., 17 (1987) 199–210.

Higgins et al., "Detection and Differentiation by Sandwich Enzyme-Linked Immunosorbent Assay of Human T-Cell Lymphotropic Virus Type III/Lymphadenopathy-Associated Virus-and Acquired Immunodeficiency Syndrome-Associated Retroviruslike Clinical Isolates" J. Clin. Microbiol., 24 (1986) 424–430.

Kanki et al., "Serologic Identification and Characterization of a Macaque T-Lymphotropic Retrovirus Closely Related to HTLV-III", Science, 228 (1985) 1199–1201.

Ferns et al., "Characterization of Monoclonal Antibodies Against the Human Immunodeficiency Virus (HIV) gag Products and Their Use in Monitoring HIV Isolat Variation", J. Gen. Virol., 68 (1987) 1543–1551.

*Primary Examiner*—Christine M. Nucker
*Attorney, Agent, or Firm*—Myron C. Cass

[57] ABSTRACT

A hybrid cell line is provided which is capable of producing monoclonal antibodies which bind to HIV core antigen P55, the precursor protein coded for the gag gene, the core protein P24 and partial breakdown products P39 and P33. The monoclonal antibody embodying the invention does not bind the P18 core protein or any HIV envelope antigens. The cell line of the invention was developed by a unique immunization protocol in which BALB/c mice were immunized over a series of multiple infusions using a select group of immunogens and a conventional myeloma cell line for fusion with the murine splenocytes harvested.

The monoclonal antibody is identified as the KC-57 antibody. This monoclonal antibody is especially useful for a solid phase immunoassay in which the monoclonal antibody is detected in its binding to HIV antigens found in a serum or plasma sample from a human patient. The cell line which produces the KC-57 monoclonal antibody has been deposited in the American Type Culture Collection, Rockville, Md. and assigned A.T.C.C. No. HB 9585.

3 Claims, No Drawings 4,888,290

MONOCLONAL ANTIBODY SPECIFIC TO HIV ANTIGENS

FIELD OF THE INVENTION

This invention relates generally to monoclonal antibodies produced by hybridoma technology and more particularly, relates to a cell line which produces a unique monoclonal antibody which recognizes epitopes of a group of gag-coded proteins of human immunodeficiency virus (HIV) isolates from a variety of different geographical locations.

BACKGROUND OF THE INVENTION

HTLV III or Human T-cell Leukemia Virus Type III, now commonly referred to as Human Immunodeficiency Virus ("HIV") is recognized to be the causative agent for human immunodeficiency syndrome or AIDS. The chronic nature of AIDS considered as approaching epidemic proportions in the United States and other countries is reflected by perfusion of studies and efforts to develop diagnostic immunoassays for reliably and consistently detecting viral antigens and antibodies to such antigens in human peripheral blood. In substantial measure, monoclonal antibody technology has been recorded to for developing such immunoassays.

HIV belongs to the retrovirus group of viruses. Retroviruses carry a positive-stranded RNA and a special enzyme called reverse transcriptase in its core which is used to convert viral RNA into DNA. This reverses the classical process of cellular transcription in which DNA is converted to RNA.

It is known that the HIV binds to T4 lymphocytes because the T4 protein on the surface of T4 lymphocytes serves as a receptor or binding site for HIV [Dalgleish AG et al., Nature 312:763–767 (1985)]. HIV also can bind to and attack other cells, such as, monocytes, tissue macrophages, and cells in the brain, spinal cord and peripheral nerves. The life cycle of HIV calls for the virus entering the host patient through sexual activity or blood transfusion, for instance, and then binding to receptors on monocytes and lymphocytes. The virus penetrates the cell and sheds its envelope or protein coat so as to expose its viral RNA core. The reverse transcriptase converts the viral RNA core to DNA which is integrated into the host cell genome. New viral particles are produced in quantity until the membrane of the host cell is ruptured to release the new viral particles in the human blood system.

HIV is comprised of protein molecules which form an enclosure membrane or envelope and a core which covers the viral RNA antigens. There are antigens expressed on the membrane and in the core materials; the core has the major portion of the proteins comprising the virus. While the general technology for producing monoclonal antibodies from cell lines is widely used and understood theoretically, the complications and variations encountered in attempting to produce specific antibodies is well recognized. Each investigation into specific monoclonal antibody development and production raises its own obstacles to successful implementation. Success or lack of success in any particular project is related in great measure to the nature of the antigen involved and techniques used to effect cell fusion and isolation of the appropriate hybridoma. These obstacles are particularly evident where production of a cell line which will produce monoclonal antibodies specific to the HIV virus is concerned. The HIV being comprised of an envelope membrane with a myriad of antigenic determinants and a core protein expressing a myriad of antigenic sites, it will be readily understood that ordinary fusion of myeloma cells and spleen cells of immunized mice will evolve an astronomical number of hybridomas and screening thereafter for specific antibodies will be a monumentally complicated exercise.

Monoclonal antibodies which recognize viral proteins of HIV isolates were studied in Ferns et al., J. Gen. Virol., 68:1543–1551 (1987-Great Britain). The monoclonal antibodies were raised against the gag proteins of the HIV. A panel of monoclonal antibodies were characterized by Western blot to establish the HIV gag proteins recognized by the monoclonal antibodies as proteins of 55,000 dalton molecular weight (p55), 24000 dalton molecular weight (p24), 18000 dalton molecular weight (P18), all core antigens.

The entire genome of the HIV has been sequenced in the study of Serki et al., Proc. Natl. Acad. Sci., 80:3618–3622 (1983). This study showed the various glycosylated proteins of the HIV envelope genes and that the core proteins are not glycosylated proteins. The study of Ferns et al., supra, shows that the glycosylated proteins of the HIV envelope gene are identified as gp 160, indicating a molecular weight of 160,000 daltons, gp 120, indicating a molecular weight of 120,000 daltons and gp 41, indicating a molecular weight of 41,000 daltons.

Diagnostic tests commercially available at this time utilizing monoclonal antibodies to determine whether a person having the AIDS disease or has been immunologically exposed to the virus can be identified have been less than successful. Diagnosis of the disease is complicated by the fact that extended periods of incubation are required before symptoms of the disease are expressed. The highly infectious nature of the disease and the fact that its cure presently is not within scientific capability also increases the difficulty of investigating live virus and its adverse affect on the human immune system so that successful diagnostic tests can be developed.

An object of this invention is to provide a hybridoma or hybrid cell line which produces a novel monoclonal antibody which binds to selective major proteins in the core. This monoclonal antibody recognizes a common epitope of certain HIV core antigens consistently and reliably so that said antibody can be employed in immunoassays to track HIV viral antigens in a human physiological serum sample with great accuracy. This monoclonal antibody does not bind HIV envelope antigens.

SUMMARY OF THE INVENTION

A cell line developed by hybridoma technology which can produce a monoclonal antibody capable of binding to HIV core antigen to p55, the precursor protein coded for the gag gene, the core protein p24 and partial breakdown products p39 and p33. The monoclonal antibody embodying the invention did not bind the p18 core protein or any HIV envelope antigens. The monoclonal antibody recognizes a common epitope on the p55, p24, p39 and p33 antigens which is identified herein as "KC-57" antigen.

The cell line of the invention was developed by a unique immunization protocol in which BALB/c mice were immunized over a series of multiple infusions using a select group of immunogens and a conventional myeloma cell line for fusion with the murine splenocytes harvested.

STATEMENT OF DEPOSIT

A cell line which produces the KC-57 monoclonal antibody corresponding to this invention has been deposited in the American Type Culture Collection, 12301 Parklawn Drive, Rockville, M.D. 20852 on Nov. 6, 1987, concurrently with the filing of this patent application. The cell line was assigned A.T.T.C. No. HB9585.

DESCRIPTION OF SPECIFIC EMBODIMENT

Materials & Methods

Viral Isolates.

Antigens for the immunization of mice were prepared from a Lymphadenopathy virus (LAV) infected cell line. Whole virus was isolated from culture supernatants by size-exclusion chromatography. A viral extract was also prepared from culture supernatants, by lysis of LAV with Triton X-100 and then absorption over a lentil lectin affinity column. The antigen eluted by methyl-alpha,-D mannopyranoside was shown by Western blot analysis to be primarily viral envelope (gp160/120), with some core antigen (p55, p24) being present.

Production of Hybridoma Cell Lines.

Male BALB/c mice were immunized intraperitoneally with an isolated LAV infected cell line in complete Freund's adjuvant. The mice then received three additional injections of purified virus in suspensions of incomplete Freund's adjuvant, i.p., each injection spaced one week apart. These injections were followed by three immunizations one week apart of gp160/120 viral extract. Three days after the third injection of gp160/120, the spleen of one mouse was removed, and a cell suspension was made. The spleen cells were then fused with SP2/0-Ag14 mouse myeloma cells, in polyethylene glycol 1500. The fused cells were plated into 96-well tissue culture plates, and antibody-producing hybridomas selected for with HAT (Hypozanthine-aminopterine-thymidine) media. (Nature 256: 495–497, 1975).

Screening of Colonies.

Colonies producing antibody to HIV core antigens were identifed by a capture ELISA. Human antibodies which recognize the HIV core antigen were absorbed onto 96-well polystyrene assay plates. After blocking non-specific binding sites with bovine serum albumin, detergent-disrupted LAV was incubated with the assay plates. The plates were then washed and conditioned media from each individual hybridoma colonies was added to an assay well. After incubation, the plates were washed, and a single composition of peroxidase-conjugated goat anti-mouse antibody which contained a mixture of antibodies to IgG, IgA and IgM antibody which contained was added and incubated. The wells were next washed, and the substrate tetramethylbenzidine (TMB) added. The reaction was stopped with $H_2SO_4$, and the absorbance was measured at 450 nm. Positive colonies including KC-57 were identified as having an absorbance at least 3 times higher than the negative central absorbance. Positive colonies were expanded, cloned in soft agar, and then injected into pristane-primed BALB/c mice for the production of antibody-containing ascites fluid.

Characterization of KC-57.

Immunogluobulin subclass of KC-57 was determined by Ouchterlony double diffusion to be murine IgG1. Western blotting was performed to determine molecular weights of antigens recognized by KC-57. Lysates of LAV infected cells were employed as the source of antigen for this analysis. A negative control for antigen were lysates of uninfected T cells. The control preparation demonstrated no reactivity with KC-57. The internal molecular weight markers used were fibrinogen (340,000), fibronectin (440,000), myosin (200,000), beta-galactosidase (116,000), phosphorylase B (92,500), bovine albumin (66,000), ovalbumin (43,000), carbonic hydrase (30,000), trypsin inhibitor (20,100) and alphalactalbumin (14,000). Following incubation of the nitrocellulose strips with KC-57, an $^{125}I$-goat anti-mouse antibody was used to detect the HIV antigens recognized by the monoclonal antibody. HIV associated core antigens p55 and p24, as well as p39 and p33 which may be cleavage products of p55, are recognized by KC-57. Reactivity with p18 was not seen and neither were any HIV envelope antigens.

Analysis of the cell surface expression of the HIV associated antigens recognized by KC-57 was performed by EPICS flow cytometer analysis, an instrument from Coulter Corporation, Hialeah, Fla. Incubation of LAV infected cells with KC-57 was followed by an incubation with goat anti-mouse FITC conjugate. No reactivity of KC-57 was demonstrated with antigenic determinants on the surface of the live HIV infected cells.

Expression of cytoplasmic HIV core related antigens was performed using acetone fixed LAV infected cells. Additionally, uninfected, HTLV-I infected and HTLV-II infected lymphocytes were obtained and prepared in an identical manner. Following incubation with KC-57, goat anti-mouse FITC conjugate was used to detect specific reactivity. No reactivity was demonstrated against uninfected, HTLV-I infected, or HTLV-II infected cells. KC-57 reacted specifically with core related antigens present in the cytoplasm of the fixed HIV infected lymphocytes.

An antigen capture EIA, employing KC-57 as the capture antibody, was developed. Purified KC-57 was solid-phased onto 96 well assay plates and blocked with BSA. The source of HIV antigen was detergent lysed culture supernatant from LAV infected lymphocytes. Following incubation and washing, biotin labeled human anti-HIV core antibody was added, incubated and washed. Next was the addition of streptavidin peroxidase with subsequent incubation. Following a final wash, TMB was added and incubated. The reaction was stopped by the addition of sulphuric acid. Absorbance was read at a wavelength of 450 nanometers. Utilizing this procedure, positive results were obtained with nine individual isolates of HIV grown in tissue culture. Antigen used to determine this reactivity was detergent lysed culture supernatant. No reactivity was seen with supernatant from uninfected cells. This data is presented in Table 3 which follows.

The KC-57 monoclonal antibody is especially useful for a solid phase immunoassay in which said monoclonal antibody is coated on a solid surface, such as the well of a microtiter plate and reacted in a controlled protocol with a human physiological fluid sample. The assay methodology may be of the ELISA type in which the KC-57 monoclonal antibody is detected in its binding to HIV antigens found in the sample. Such an immunoassay is disclosed in the co-pending patent application titled Enzyme Immunoassay For Detecting HIV Antigens in Human Sera owned by the same assignee and filed concurrently herewith.

TABLE 1

| KC-57 HIV ANTIGEN CAPTURE ELISA | | |
|---|---|---|
| HIV ISOLATE | REGION ISOLATED | RESULTS |
| LAV | France | + |
| BAGAL | New York City | + |
| 1265 D13 | Atlanta | + |
| Z34 | Zaire | + |
| SDR | San Francisco | + |
| 2153 D16 | New York City | + |
| 121886-1 | Bethesda | + |
| 1272 D21 | Chicago | + |

Table 1 demonstrates that the HIV antigen assay utilizing the KC-57 monoclonal antibody as a capture phase and human anti-HIV antibody as the detector phase identified all strains listed as being positive for HIV antigen content.

TABLE 2

| SPECIFICITY OF KC-57 MONOCLONAL ANTIBODY | | |
|---|---|---|
| Infectious Agent | # Tested | # Positive |
| EBV | 2 | 0 |
| HTLV I | 2 | 0 |
| HTLV II | 2 | 0 |
| HSV I | 2 | 0 |
| HSV II | 2 | 0 |

TABLE 2-continued

| SPECIFICITY OF KC-57 MONOCLONAL ANTIBODY | | |
|---|---|---|
| Infectious Agent | # Tested | # Positive |
| CMV | 2 | 0 |
| Chlamydia | 2 | 0 |

The above table demonstrates the reactivity of KC-57 antibody against other infectious agents when run in the HIV Antigen Assay. No reactivity is seen with any of these agents.

The above table demonstrates the reactivity of KC-57 monoclonal antibody against other infectious agents when used as the capture antibody in the HIV Antigen Assay described in said HIV application.

We claim:

1. A hybridoma cell line which produces a monoclonal antibody which specifically binds to an epitope of the KC-57 antigen and is on deposit with the American Type Culture Collection, Rockville, Md., and assigned A.T.C.C. No. HB 9585.

2. A monoclonal antibody produced from the hybridoma cell line sample on deposit with the American Type Culture Collection, Rockveille, Md. and assigned A.T.C.C. No. HB 9585.

3. A monoclonal antibody which specifically binds to an antigenic determinant of the HIV p55, p24, p39 and p33 core antigens identified as KC-57, and which monoclonal antibody does not have binding specificity with respect to the HIV core antigen p18 and HIV envelope antigens.

* * * * *